United States Patent
Xu et al.

(10) Patent No.: US 7,620,223 B2
(45) Date of Patent: Nov. 17, 2009

(54) METHOD AND SYSTEM FOR REGISTERING PRE-PROCEDURAL IMAGES WITH INTRA-PROCEDURAL IMAGES USING A PRE-COMPUTED KNOWLEDGE BASE

(75) Inventors: Chenyang Xu, Allentown, NJ (US); Nassir Navab, Plainsboro, NJ (US); Frank Sauer, Princeton, NJ (US); Ali Khamene, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 595 days.

(21) Appl. No.: 11/104,831

(22) Filed: Apr. 13, 2005

(65) Prior Publication Data

US 2005/0272991 A1  Dec. 8, 2005

Related U.S. Application Data

(60) Provisional application No. 60/564,508, filed on Apr. 22, 2004.

(51) Int. Cl.
*G06K 9/00* (2006.01)
(52) U.S. Cl. .................. 382/128; 382/131; 382/132
(58) Field of Classification Search ............... 382/128, 382/131, 132
See application file for complete search history.

(56) References Cited

U.S. PATENT DOCUMENTS

| 6,347,240 B1* | 2/2002 | Foley et al. ............. 600/426 |
| 6,614,453 B1* | 9/2003 | Suri et al. .............. 715/764 |
| 6,837,892 B2* | 1/2005 | Shoham ................. 606/130 |
| 2002/0077543 A1* | 6/2002 | Grzeszczuk et al. ....... 600/424 |
| 2004/0215071 A1* | 10/2004 | Frank et al. ............. 600/407 |

OTHER PUBLICATIONS

Gluckman, J. "On the use of marginal statistics of subband images" Proceedings of Ninth IEEE International Conference on Computer Vision, 2003. vol. 1, 448-453.*

Lille Zollei, "2D-3D Rigid-Body Registration of X-Ray Fluoroscopy and CT Images", Masters Thesis, MIT AI Lab, Aug. 2001.

* cited by examiner

*Primary Examiner*—Samir A Ahmed
*Assistant Examiner*—Li Liu

(57) ABSTRACT

A system and method for registering pre-operative images of an object with an intra-operative image of the object is disclosed. Prior to an operative procedure, Digitally Reconstructed Radiographs (DRRs) are generated for the pre-operative images of each individual patient. Signatures are extracted from the DRRs. The signatures are stored in a knowledge base. During the operative procedure, a signature is extracted from the intra-operative image. The intra-operative signature is compared to the stored pre-operative signatures. A pre-operative image having a best signature match to the intra-operative signature is retrieved. The retrieved pre-operative image is registered with the intra-operative image.

24 Claims, 3 Drawing Sheets

METHOD AND SYSTEM FOR REGISTERING PRE-PROCEDURAL IMAGES WITH INTRA-PROCEDURAL IMAGES USING A PRE-COMPUTED KNOWLEDGE BASE

CROSS REFERENCE TO RELATED APPLICATIONS

This application claims the benefit of U.S. Provisional Patent Application Ser. No. 60/564,508, filed Apr. 22, 2004, which is incorporated by reference in its entirety.

FIELD OF THE INVENTION

The present invention is directed to a method and system for registering pre-procedural images with intra-procedural images, and more particularly, to a system and method for registering pre-procedural images with intra-procedural images using a pre-computed knowledge base of the pre-procedural image data.

BACKGROUND OF THE INVENTION

Medical professionals have recently been exploiting pre-operative or pre-procedural images and intra-operative or intra-procedural images to provide a more useful and inexpensive registered image of an organ, which is the subject of a minimally invasive therapeutic intervention. For example, a tumor can be imaged both pre-operatively using a CT system and intra-operatively using an X-ray system. Digital Reconstructed Radiographs (DRRs) are reconstructed from the CT images to model the X-ray images. The pre-operative DRRs and the intra-operative images are registered and merged to provide both structural and functional information about the tumor and the effected organ. Subsequent images taken intra-operatively using the X-ray system can then be merged with the pre-operative image over time to assist the physician. The pre-operative images can provide detail about the anatomy that is the subject of the procedure. Three dimensional image modalities such as Computed Tomography (CT) and Magnetic Resonance Imaging (MRI) contain high resolution information about the imaged anatomy.

The intra-operative images are typically two dimensional images that are available to provide the physician with an indication of the current state of the anatomy in question. X-ray and fluoroscopy images are typically used for these purposes. Two dimensional (2D) images take significantly less time to acquire than three dimensional (3D) images and are less intrusive to the physician. However the resolution and detail of the 2D images are inferior to that of its 3D counterpart. By combining the pre-operative and intra-operative images by registering the two images, the physician can have the benefit of the detail of the pre-operative images and the current state of the patient via the intra-operative images.

Conventional registration of a projection image to a volumetric data set involves three steps. First, computation of a simulated projection image (e.g., Digitally Reconstructed Radiographs (DRRs)) is performed given the current relative position of an X-ray source image and the volume. Second, computation of the similarity measure and/or difference measure quantifying a metric for comparing the X-ray or portal image to the DRR is performed. Third, an optimization scheme is employed which searches through the parameter space (e.g., six dimensional rigid body motion) in order to maximize the similarity measure or minimize the difference measure. Once the optimum position is found, the DRR image should match the X-ray image.

The registration of two dimensional (2D) and three dimensional (3D) images is a well-known technique. It is important to compute the DRR so that it matches the real X-ray image in terms of both brightness and contrast. In addition, a well-behaved similarity measure should be chosen that can robustly characterize a metric for the images. In order to make such an algorithm practical, the computational time has to be reduced. Based on the current state of the art, implementation of such techniques for typical 3D volume data sets have a computation time of a few minutes. Most of the computation time is spent on generating DRRs. Another factor affecting the computation time is the number of iterations that have to be computed.

One approach for reducing the computation time is to randomly sample the DRRs and only use those samples for performing computations, thereby reducing the computational complexity. However, one drawback to this approach is that the robustness of the results is compromised since less information is available to the optimizer to take an accurate step toward the global solution. For many practical applications, especially interventional scenarios, registration time is crucial. It would be desirable to be able to perform registrations in real-time or close to real-time.

SUMMARY OF THE INVENTION

The present invention is directed to a system and method for registering pre-operative images of an object with an intra-operative image of the object. Prior to an operative procedure, Digitally Reconstructed Radiographs (DRRs) are generated for the pre-operative images of each individual patient. Signatures are extracted from the DRRs. The signatures are stored in a knowledge base. During the operative procedure, a signature is extracted from the intra-operative image. The intra-operative signature is compared to the stored pre-operative signatures. A pre-operative image having a best signature match to the intra-operative signature is retrieved. The retrieved pre-operative image is registered with the intra-operative image.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a method for registering pre-operative high resolution images with intra-operative low resolution images. In accordance with the present invention, Digitally Reconstructed Radiographs (DRRs) at various poses are precomputed for the pre-operative images of each individual patient and stored with the images in a database. Because the DRRs are computed prior to the interventional procedure most of the complexity and computation time has been eliminated from the typical registration process. As such, registration of a pre-operative and intra-operative image can be processed in an extremely fast and efficient manner. Prior art registration techniques can take up to a minute to compute. By implementing the method of the present invention, registration can be accomplished in real-time (up to 20 frame/s).

Figure 1:
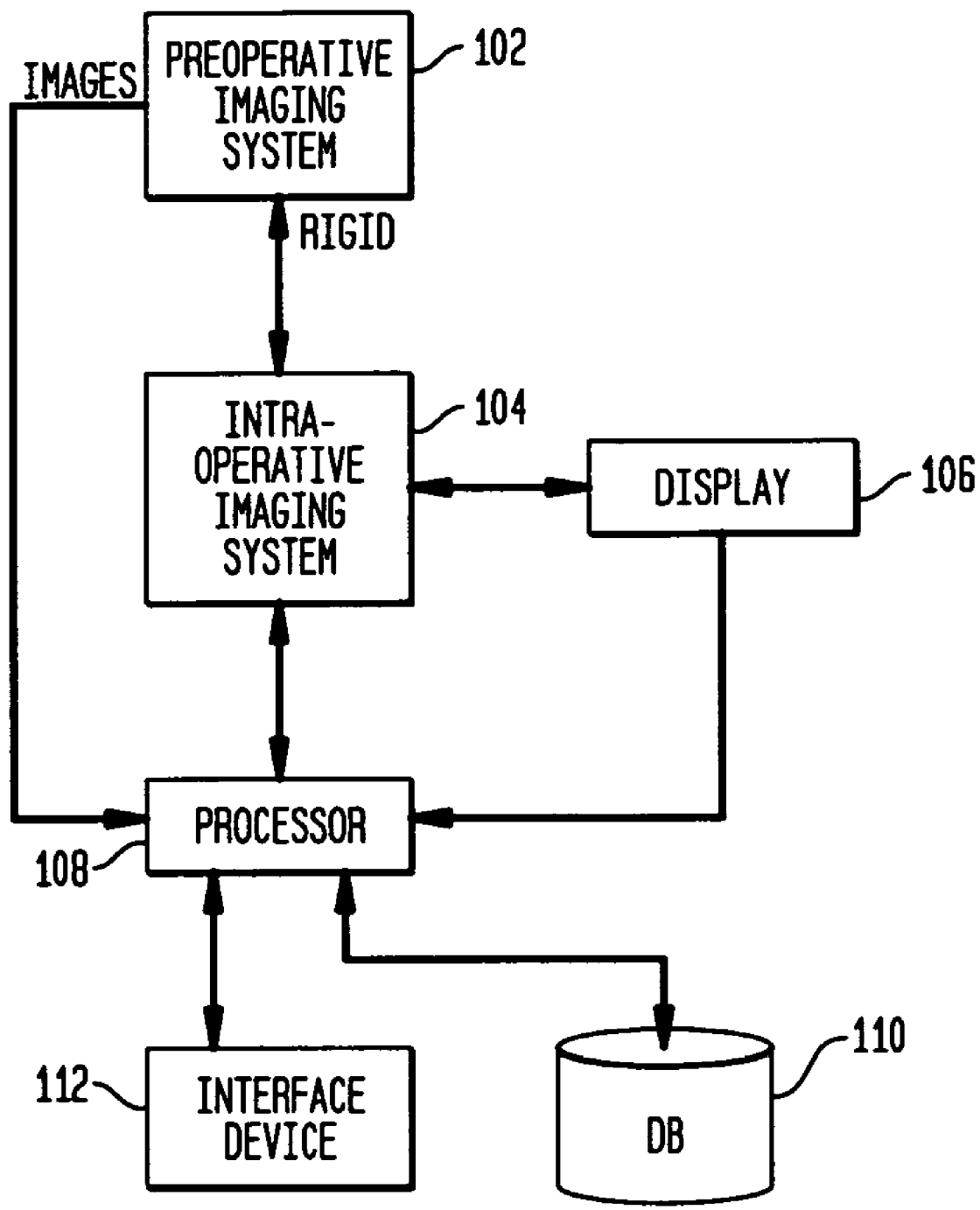
FIG. 1 is a schematic block diagram of an illustrative system for implementing a method of registering pre-operative images with intra-operative images in accordance with the present invention.

FIG. 1 illustrates a schematic block diagram of an illustrative system for implementing the method of the present invention. The present invention exploits the pre-operative images and intra-operative images to provide a more useful and inexpensive registered image of an organ, which is the subject of a minimally invasive therapeutic intervention. For example, a tumor can be imaged both pre-operatively using a three dimensional imaging system, such a Computed Tomography (CT) system or a Magnetic Resonance Imaging (MRI) system and inter-operatively using a two dimensional imaging system such as an X-ray or fluoroscopy device. The images are registered and merged to provide both structural and functional information about the tumor and the effected organ. Subsequent images taken intra-operatively can then be merged with the pre-operative image over time to assist the physician.

In accordance with the present invention, a database 110 is generated based on the pre-operative volumetric data. The constructed database 110 includes the position information (e.g., pose) of each entry and also a set of signatures or features pertaining to the particular image, which are extracted from the digitally reconstructed radiographs (i.e., DRR) at the same position. Examples of such signatures include intensity histogram, invariants derived from multi-scale Gaussian filters or Gabor filters, the image itself and so on. These features could be used in a hierarchical manner ordered by their query efficiency. As will be described in more detail hereinafter, matching of the interventional (intra-operative) image space to the pre-operative diagnostic space is then reduced to pose and retrieval of the extracted signature of the current projection image within the database 110.

An image of a desired tissue region or an organ is obtained by employing an imaging system 102 such as, for example, a CT or MRI device. Data is collected for images of the tissue region or organ and stored for further processing by processor 108. These images are obtained prior to any operative procedure. Other organs or internal structures may also be imaged as needed. The images are then reconstructed into DRRs and the above knowledge base is generated and stored in database 110 for each DRR.

Images of the same desired tissue region or organ are then obtained by employing an intra-operative imaging system 104 which may also be an X-ray device or linear accelerator. During the operative procedure, an initial image is obtained and stored in processor 108. Rigid registration of the image from the intra-operative imaging system and the images from the pre-operative imaging system is performed. Preferably, the image taken by the intra-operative imaging system is matched to an image taken pre-operatively that has the same pose and is in a relatively similar state. For example, an internal organ that is imaged should be in approximately the same state for both imaging processes to ensure proper registration. Identifying pre-operative images having the same pose and signatures is greatly simplified because a match can easily be found by performing a look up in the knowledge base.

Two scenarios can be considered. First in abdominal and thoracic procedures, the rigidity of the internal organ movement can be assured using either breath-hold techniques or gating techniques (e.g., both the pre-procedural and first set of inter-procedural image is taken at the full inhalation). Second for neurosurgical procedures, only after craniotomy, there exists some deformable movement of the structure, which is so-called brain-shift. Therefore, the rigidity assumption for this stage is quite reasonable.

As indicated above, the image data from the preoperative-imaging system 102 and the intra-operative imaging system 104 are input to processor 108. Processor 108 may include a Graphical User Interface (GUI), which permits a user to manually draw a border or contour around a region of interest in the images. Alternatively, a segmentation algorithm may be employed to differentiate regions of interest and draw contours for images without user interaction. Segmentation algorithms known to those skilled in the art may be employed. Database 110 stores the images.

A display 106 is included for displaying the images and displaying the registered images. An interface device or devices 112 are also included such as a keyboard, mouse or other devices known in the art.

Figure 2:
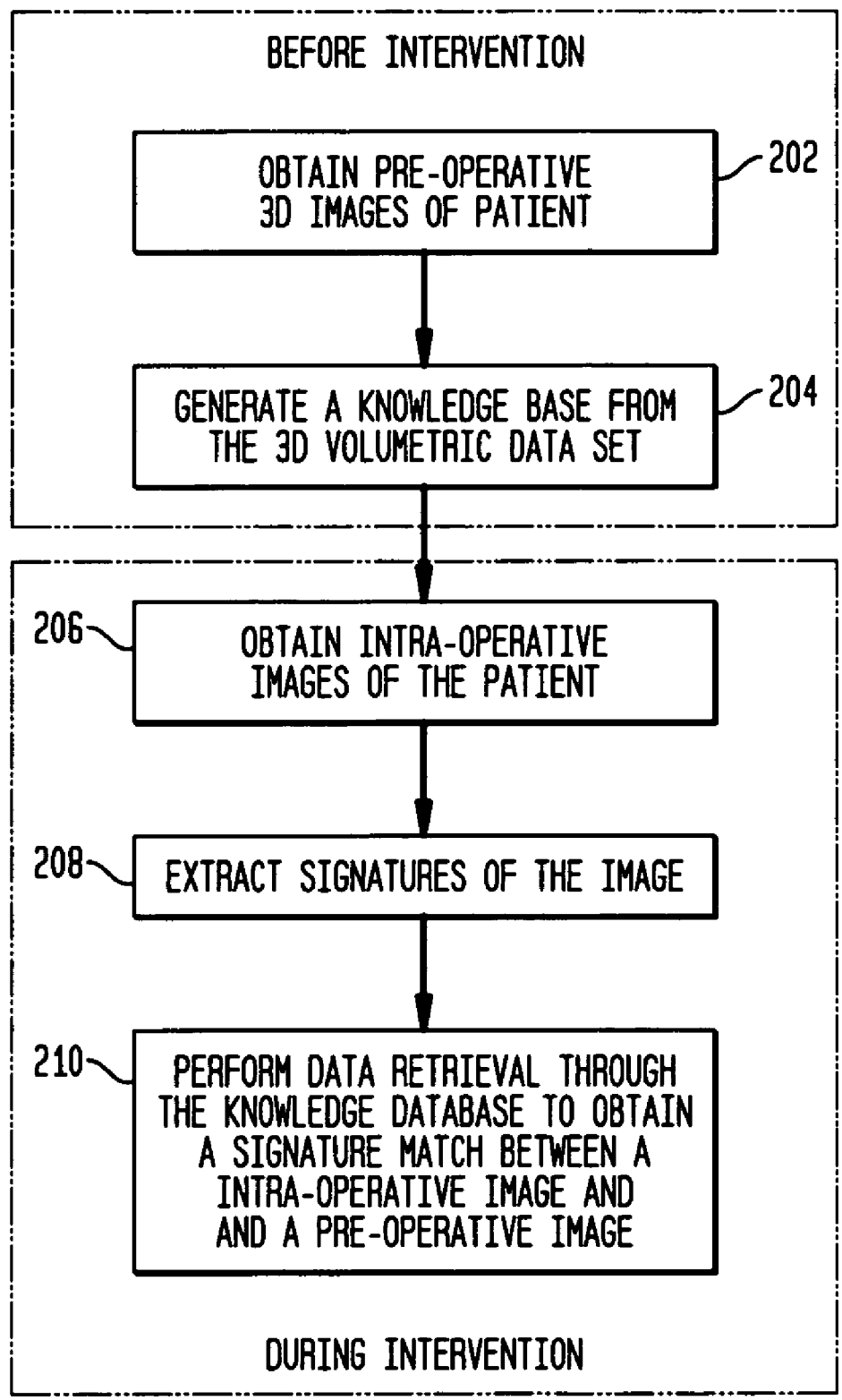
FIG. 2 is a flow diagram illustrating a method for registering pre-operative images with intra-operative images in accordance with the present invention.

FIG. 2 is a flow chart that illustrates an exemplary method for registering pre-operative images with intra-operative images in accordance with the present invention. Pre-operative images of a patient are obtained using a three dimensional (3D) imaging system (step 202). A knowledge base is generated from the pre-operative volumetric data set associated with the 3D images (step 204). The knowledge base comprises thousands of DRR images that are computed from the volume for all the specified poses using standard DRR algorithms implemented either by software or by hardware. Each pose is defined by the projection matrix that mimics the actual projection matrix of the targeted C-Arm system for 2D fluoro image acquisition. The pose is varied with a specified sampling resolution such that all the orientations in 3D are sampled uniformly as much as possible.

The knowledge base has entries encoding information about the DRR at various poses and the actual position and orientation of the object being imaged. Typically these images are used in medical applications for examining various human organs for medical conditions or tumors. The type of information that is extracted from the DRRs at each pose may vary depending upon the application. It is also possible to save the whole DRR image along with the pose information as one data entry. Each data entry in the knowledge base is a compact representation of a DRR at a certain pose. Features or signatures of the DRR can also be stored such as the maximum intensity marginals of the image.

The knowledge base is arranged in a tree-like structure and is arranged based on the position and orientation information in which the neighborhoods can be defined. In accordance with the present invention, the knowledge base is set up based on pose. Similar poses are assigned to the same neighborhood. This will make the retrieval of an entry at the corresponding pose faster and easier.

The knowledge base has to be large enough to cover discrepancies of the parameter space up to a certain degree. The larger the coverage of the knowledge base in terms of pose, the larger the operating base of the algorithm as a whole. The spacing and/or resolution of the poses stored in the knowledge base can vary depending upon the application. One implementation may consider having a more compact knowledge base at the expense of larger spacing among the poses (i.e., lower pose resolution). This kind of implementation is then coupled with a refinement step where a conventional approach can be used to achieve further accuracy and to compensate for the lost resolution in the knowledge base.

Next intra-operative images are taken of the same patient (step 206). An X-ray or fluoroscopy device is used to take the images. Signatures of the image are extracted in the same way that that knowledge base was generated (step 208). A metric is defined to provide a distance measure among the data entries and the given intra-operative image. The definition of the distance measure depends upon the way that the signatures are defined. For simple metric such as histogram, a sum of squared distance could be used, whereas for image metric derived from Gaussian and Gabor filtering, one can use distance measure derived from cross correlation and mutual information of two images. Data retrieval is performed through the knowledge base in order to retrieve the best signature match of a pre-operative image with the current intra-operative image (step 210). The pose of the resultant entry would carry the registration information. Since the generation of the knowledge base is computed prior to obtaining the intra-operative images, extraction of the signatures of the X-ray images and search and retrieval of the volumetric data in the database can be performed very efficiently.

Figure 3:
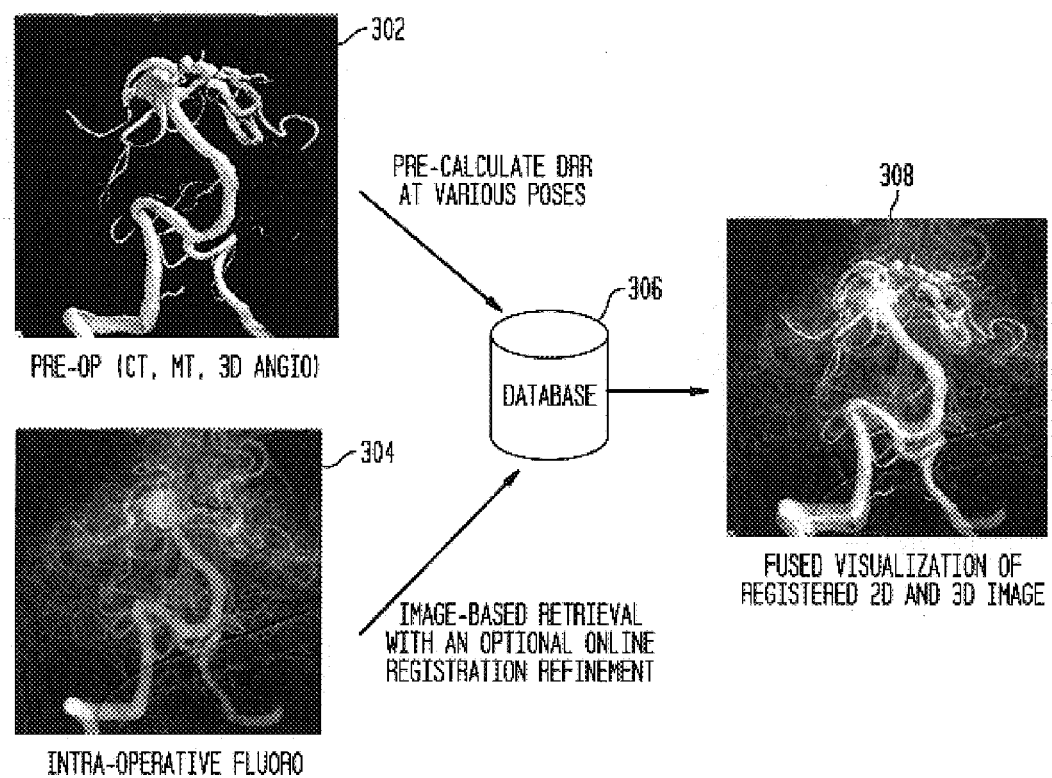
FIG. 3 illustrates a method for registering a pre-operative and intra-operative image in accordance with the present invention.

FIG. 3 illustrates the method of registering pre-operative images with intra-operative images in accordance with the present invention. Prior to a medical procedure, 3D pre-operative images 302 of the patient, in this case carotid vessels, are obtained in the manner described above. DRRs are pre-calculated at various poses for the images and stored in database 306. Next during the medical procedure, 2D intra-operative images 304 of the carotid vessels are taken. Preferably, the positioning and angle in which the intra-operative images are taken are the same as those for the pre-operative images. These images are also sent to database 306. Next, the pre-operative images are retrieved from the database and a real-time online registration of the pre-operative and intra-operative images occurs. The resulting registered image 308 is displayed which is essentially a fused version of the 2D and 3D images.

Having described embodiments for a method for registering pre-operative DRRs with intra-operative images, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A computer implemented method for registering pre-operative images of an object with an intra-operative image of the object during an operative procedure, said method performed by the computer comprising the steps of:
   providing a knowledge base extracted from pre-operative 3D images of an anatomical region of a patient, said knowledge base including 2D digitally reconstructed radiographs (DRRs) computed from said pre-operative 3D images for a plurality of poses and a set of signatures indicative of each said DRR;
   acquiring a 2D intra-operative image of the anatomical region of the patient;
   extracting a signature from the intra-operative image;
   comparing the intra-operative signature to the stored pre-operative signatures;
   retrieving a pre-operative image having a best signature match to the intra-operative signature; and
   registering the retrieved best matching pre-operative image with the intra-operative image.

2. The method of claim 1, wherein the pre-operative images are computed tomography images.

3. The method of claim 1, wherein the pre-operative images are magnetic resonance images.

4. The method of claim 1, wherein the intra-operative image is an X-ray image.

5. The method of claim 1 wherein the intra-operative image is a fluoroscopy image.

6. The method of claim 1 wherein at least one signature is a histogram.

7. The method of claim 1 wherein at least one signature is an invariant derived from multiscale Gaussian filters.

8. The method of claim 1 wherein at least one signature is an invariant derived from multiscale Gabor filters.

9. The method of claim 1 wherein a distance measurement is used to compare the intra-operative signature to the pre-operative signatures.

10. The method of claim 1, wherein said registration is performed in substantially real-time.

11. The method of claim 1, wherein a pose of the retrieved best matching pre-operative image includes information needed for registration.

12. The method of claim 1 wherein a signature of the intra-operative image is extracted in the same way as the corresponding signature of an image retrieved for comparison from the knowledge base.

13. The method of claim 1, wherein the knowledge base is arranged in a tree-like structure based on pose information in which the neighborhoods can be defined, wherein similar poses are assigned to a same neighborhood,
   wherein the pose is varied with a specified sampling resolution such that all poses in 3D are sampled substantially uniformly, and
   wherein said knowledge base is adapted to be queried in a hierarchical manner.

14. A system for registering pre-operative images of an object with an intra-operative image of the object comprising:
   a two dimensional (2D) imaging system;
   a processor for performing the following steps:
      i). receiving pre-operative images generated by a three dimensional (3D) imaging system;
      ii). generating a hierarchical knowledge base from the pre-operative 3D images said knowledge base including 2D digitally reconstructed radiographs (DRRs) computed from said pre-operative 3D images;
      iii). receiving intra-operative images generated by the 2D system and extracting signatures from the images;
      iv). exacting signatures from the DRRs;
      v). comparing the intra-operative signature to the pre-operative signatures;
      vi). identifying a pre-operative image having a best signature match to the intra-operative signature; and
      vii). registering the identified pre-operative image with the intra-operative image;
   a database for storing the knowledge base of pre-operative images, and the intra-operative and registered images; and
   a display for displaying the images.

15. The system of claim 14 wherein the pre-operative images are computed tomography images.

16. The system of claim 14 wherein the pre-operative images are magnetic resonance images.

17. The system of claim 14 wherein the intra-operative image is an X-ray image.

18. The system of claim 14 wherein the intra-operative image is a fluoroscopy image.

19. The system of claim 14 wherein at least one signature is a histogram.

20. The system of claim 14 wherein at least one signature is an invariant derived from multiscale Gaussian filters.

21. The system of claim 14 wherein at least one signature is an invariant derived from multiscale Gabor filters.

22. The system of claim 14 wherein a distance measurement is used to compare the intra-operative signature to the pre-operative signatures.

23. The system of claim 14 wherein the object is a patient.

24. A program storage device readable by a computer, tangibly embodying a program of instructions executable by the computer to perform the method steps for registering pre-operative images of an object with an intra-operative image of the object, said method during an operative procedure, said method comprising the steps of:

provniding a knowledge base extracted from pre-operative 3D images of an anatomical region of a patient, said knowledge base including 2D digitally reconstructed radiographs (DRRs) computed from said pre-operative 3D images for a plurality of poses and a set of signatures indicative of each said DRR;

acquiring a 2D intra-operative image of the anatomical region of the patient;

extracting a signature from the intra-operative image;

comparing the intra-operative signature to the stored pre-operative signatures;

retrieving a pre-operative image having a best signature match to the intra-operative signature; and registering the retrieved best matching pre-operative image with the intra-operative image.

* * * * *